United States Patent [19]

Tate

[11] Patent Number: 4,480,995
[45] Date of Patent: Nov. 6, 1984

[54] APPARATUS FOR USE IN FABRICATING ORTHODONTIC APPLIANCES

[76] Inventor: Ronald L. Tate, 3230 Centennial, Sylvania, Ohio 43560

[21] Appl. No.: 534,967

[22] Filed: Sep. 22, 1983

[51] Int. Cl.$^3$ ............................................. A61C 11/00
[52] U.S. Cl. ........................................ 433/54; 433/65
[58] Field of Search ...................... 433/53, 54, 55, 56, 433/57, 58, 59, 60, 61, 62, 63, 64, 65, 66, 67

[56] References Cited

U.S. PATENT DOCUMENTS

| 1,102,741 | 7/1914 | Hardie | 433/60 |
| 2,138,254 | 11/1938 | Mink | 433/56 |
| 2,930,127 | 3/1960 | Mann et al. | 433/56 |
| 3,059,336 | 10/1962 | Windish | 433/54 |
| 3,758,096 | 9/1973 | Tregillis et al. | 433/54 |
| 4,155,163 | 5/1979 | Schwartz | 433/56 |
| 4,412,822 | 11/1983 | Blechner | 433/57 |

FOREIGN PATENT DOCUMENTS

| 448368 | 5/1948 | Canada | 433/54 |
| 960846 | 4/1950 | France | 433/65 |

*Primary Examiner*—John J. Wilson
*Attorney, Agent, or Firm*—Fraser, Barker, Purdue & Clemens

[57] ABSTRACT

The present invention relates to an improved apparatus for use in fabricating orthodontic appliances. The apparatus includes a pair of spaced apart lower and upper horizontally extending arms. The lower arm is adapted to carry a lower dental casting and the upper arm is adapted to carry an upper dental casting in facing relationship with the lower dental casting. A pair of spaced apart parallel cylindrical guide shafts extend upwardly in a generally vertical direction from the lower arm. The upper arm is attached to a mounting device utilized to support the upper arm for vertical movement toward and away from the lower arm. The mounting device includes a pair of spaced apart cooperating guide apertures for slidably receiving the guide shafts. A locking screw is provided in the mounting device for frictionally engaging one of the guide shafts for releasably securing the upper arm in a selected vertical position relative to the lower arm. A reference stop member having a pair of apertures formed therein for slidably receiving the guide shafts is positioned on the guide shafts between the lower arm and the upper arm. The stop means includes a locking screw for releasably securing the stop means on the guide shafts in a selected vertical position relative to the lower arm. The stop member is engageable with the mounting device of the upper arm for limiting the spacing between the upper arm and the lower arm.

5 Claims, 4 Drawing Figures

APPARATUS FOR USE IN FABRICATING ORTHODONTIC APPLIANCES

BACKGROUND OF THE INVENTION

The present invention relates in general to a holding device for use in fabricating orthodontic appliances and, in particular, to a device having an upper dental casting holding arm which is mounted for vertical movement toward and away from a lower dental casting holding arm.

Several types of orthodontic holding devices have been proposed to provide selective vertical movement between an upper dental casting and a lower dental casting. One such device is disclosed in U.S. Pat. No. 3,059,336 to Windish. The device in the Windish patent comprises a horizontally extending upper arm which is adapted for vertical movement toward and away from a horizontally extending lower arm. A pair of spaced apart parallel guide pins extend upwardly from the lower arm and are adapted to be inserted within corresponding guide holes provided in an upper block attached to the upper arm. A locking screw is carried by the upper block and is utilized to frictionally engage one of the guide pins for maintaining the upper arm in a selected vertical position relative to the lower arm.

Another type of orthodontic holding device is manufactured by Knochen Dental. The Knochen device includes a horizontally extending lower arm having an upwardly extending guide member at one end thereof. The guide member is perpendicular to the lower arm and has a generally rectangular cross section. A horizontally extending upper arm is attached to a mounting device having a rectangular slot formed therein for slidably receiving the upstanding guide member. A locking screw is provided in the mounting device for frictionally engaging the guide member for locking the upper arm in a fixed vertical position relative to the lower arm. Also, a reference stop means is positioned on the guide member and is used to limit the minimum vertical spacing between the upper and lower arms.

Other types of orthodontic holding devices are disclosed in U.S. Pat. Nos. 2,930,127 and 3,758,096.

SUMMARY OF THE INVENTION

The present invention concerns an improved apparatus for use in fabricating orthodontic appliances. The apparatus includes a pair of spaced apart lower and upper horizontally extending arms. The lower arm is adapted to carry a lower dental casting, and the upper arm is adapted to carry an upper dental casting in facing relationship with the lower dental casting. A guide means is secured to the lower arm and extends upwardly in a generally vertical direction. Means are provided for mounting the upper arm on the guide means for vertical movement toward and away from the lower arm. The mounting means includes means for preventing any pivotally movement of the upper arm relative to the lower arm above the guide means when the upper arm is spaced less than a predetermined distance from the lower arm, and permits pivotal movement of the upper arm relative to the lower arm about the guide means when the upper arm is spaced more than the predetermined distance from the lower arm.

In the preferred embodiment of the invention, the guide means includes a pair of spaced apart, parallel cylindrical guide pins which extend upwardly in a generally vertical direction from the lower arm. The means for mounting the upper arm on the guide shafts includes a pair of spaced apart cooperating guide apertures for slidably receiving the guide shafts. Also, means are provided for releasably securing the upper arm on the guide shafts in a selected vertical position relative to the lower arm.

The preferred embodiment of the invention further includes a reference stop means having at least one aperture formed therein for slidably receiving at least one of the guide shafts. The reference stop means is positioned on the one guide shaft between the lower arm and the upper arm and includes means for releasably securing the stop means on the one guide shaft in a selected vertical position relative to the lower arm. The stop means is engageable with the mounting means for limiting the spacing minimum between the upper arm and the lower arm.

It has been found that an apparatus having the structure of the present invention provides a structure wherein precise vertical movement can be obtained between the lower and upper arm. Also, it has been found that the present invention provides a structure which can be easily disassembled and cleaned after the associated dental castings have been removed.

BRIEF DESCRIPTION OF THE DRAWINGS

The above, as well as other advantages of the present invention, will become readily apparent to one skilled in the art from reading the following detailed description in conjunction with the accompanying drawings, in which.

DESCRIPTION OF THE PREFERRED EMBODIMENT

Figure 1:
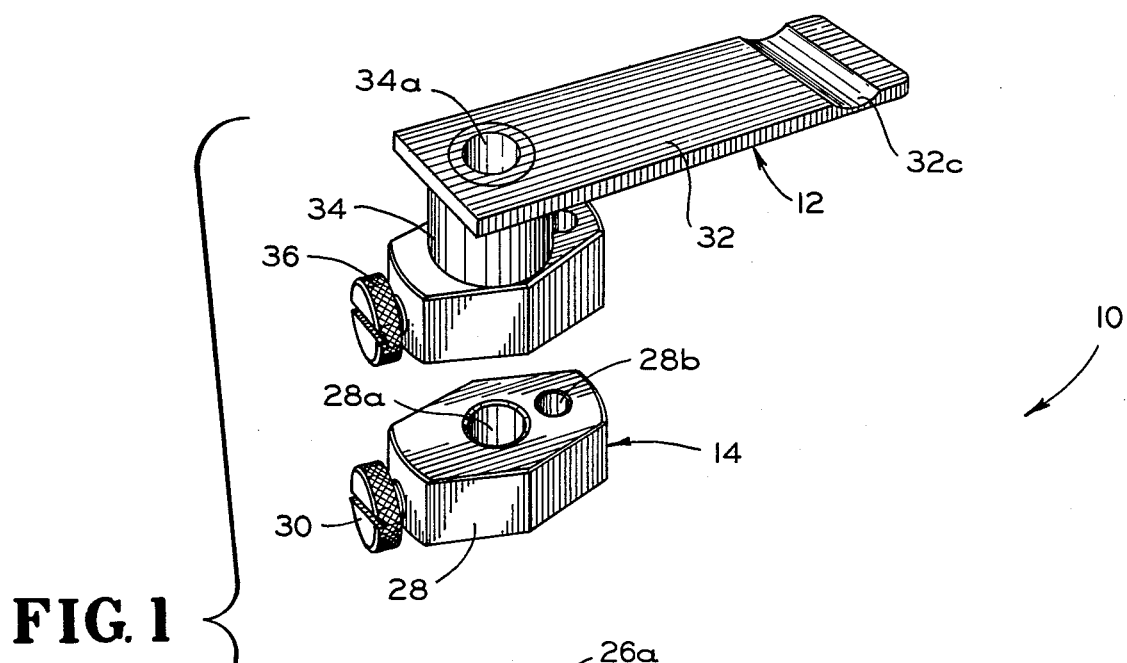
FIG. 1 is an exploded perspective view illustrating the individual components of the apparatus of the present invention.
Figure 2:
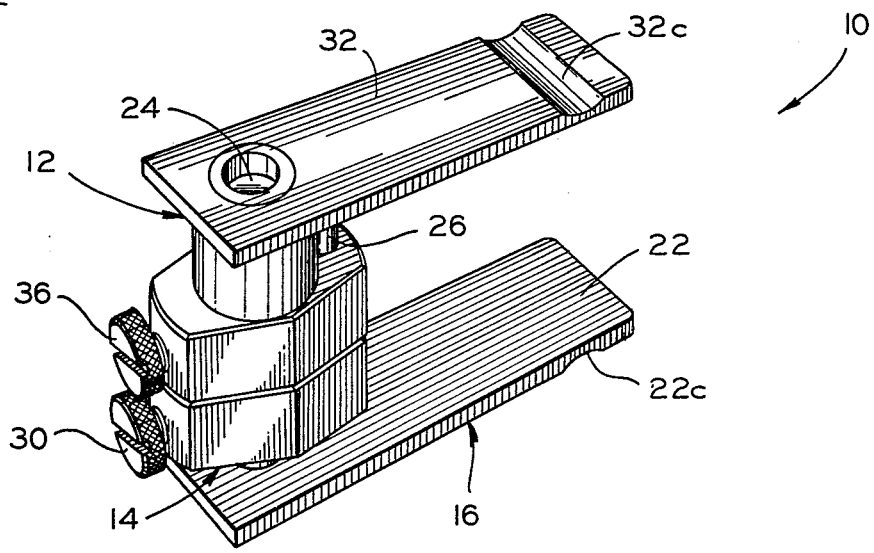
FIG. 2 is a perspective view of the apparatus of FIG. 1 shown in an assembled condition.

Referring to the drawings, there is shown an apparatus 10 embodying the features of the present invention. It should be noted at the outset of this description that, while the apparatus 10 is described for use in fabricating orthodontic appliances, it will be appreciated that the apparatus can be utilized in other dental applications such as for use in producing dental restorations, for example.

Figure 3:
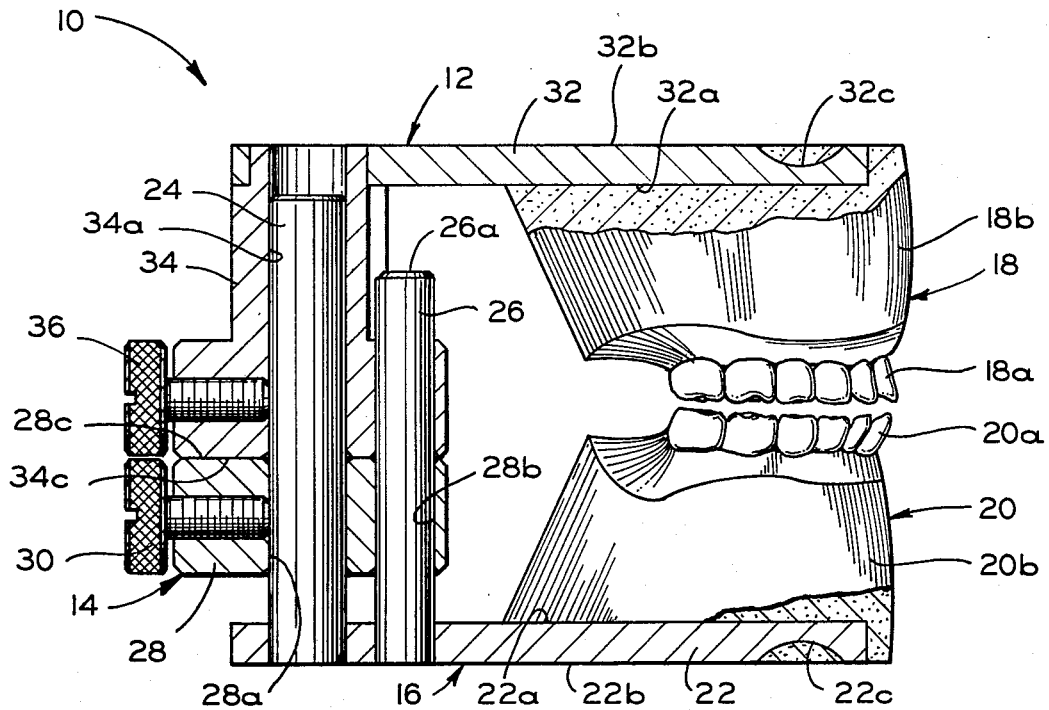
FIG. 3 is a side sectional view of the apparatus of FIG. 2 having a set of dental castings secured thereto.

Referring to FIG. 1, the apparatus 10 includes three main components, a lower arm assembly 12, a reference stop member 14, and an upper arm assembly 16. As shown in FIG. 3, the lower arm assembly 12 is adapted to carry a lower dental casting 18 which includes a model 18a of a patient's lower teeth secured to a plaster cast 18b. The upper arm assembly 16 is adapted to carry an upper dental casting 20 in facing relationship to the lower dental casting 18. The upper dental casting includes a model 20a of the patient's upper teeth secured to a plaster cast 20b.

The lower arm assembly 12 includes a horizontally extending arm 22 having a generally planar upper surface 22a and a generally planar lower surface 22b. An arcuate groove 22c is formed in the lower surface 22b near the outer end of the lower arm 22. The groove 22c is used to facilitate the securing of the lower dental casting 18 to the lower arm 22 by receiving a portion of the plaster cast 18b. The inner end of the lower arm 22 is provided with a pair of spaced apart, parallel cylindrical guide shafts 24 and 26. In the preferred embodiment of the invention, the cylindrical guide shaft 24 is of a diameter slightly larger than the diameter of the guide shaft 26 and extends upwardly past the upper end of the guide shaft 26.

The reference stop member 14 includes a main body portion 28 having a pair of spaced apart apertures 28a and 28b adapted to receive the guide shafts 24 and 26, respectively. A locking screw 30 extends transversely relative to the aperture 28a and is adapted to frictionally engage the guide shaft 24 for releasably securing the stop member 14 in a selected vertical position along the guide shafts 24 and 26. As will be discussed, the stop member 14 enables the technician to set a predetermined minimum spacing between the upper and lower arm assemblies 12 and 16.

The upper arm assembly 16 includes a horizontally extending upper arm 32 having a relatively planar lower surface 32a and a relatively planar upper surface 32b. An arcuate groove 32c, which functions in a manner similar to the groove 22c of the lower arm 22, is formed in the upper surface 30b at the outer end of the upper arm 32. The inner end of the arm 32 is attached to a mounting device 34 which is utilized to support the upper arm 32 for vertical movement toward and away from the lower arm 22. The mounting device 34 is provided with a pair of spaced apart guide apertures 34a and 34b which are adapted to receive the guide shafts 24 and 26, respectively. A locking screw 36 is carried by the mounting device 34 and is adapted to frictionally engage the guide shaft 24 for releasably securing the upper arm 32 in a selected vertical position along the guide shafts 24 and 26.

As shown in FIG. 3, a lower surface 34c of the mounting device 34 engages an upper surface 28c of the main body portion 28 of the stop member 14 to prevent further downward movement of the upper arm relative to the lower arm. Thus, the stop member 14 enables the technician to set a predetermined minimum spacing M between the upper arm 32 and the lower arm 22.

Figure 4:
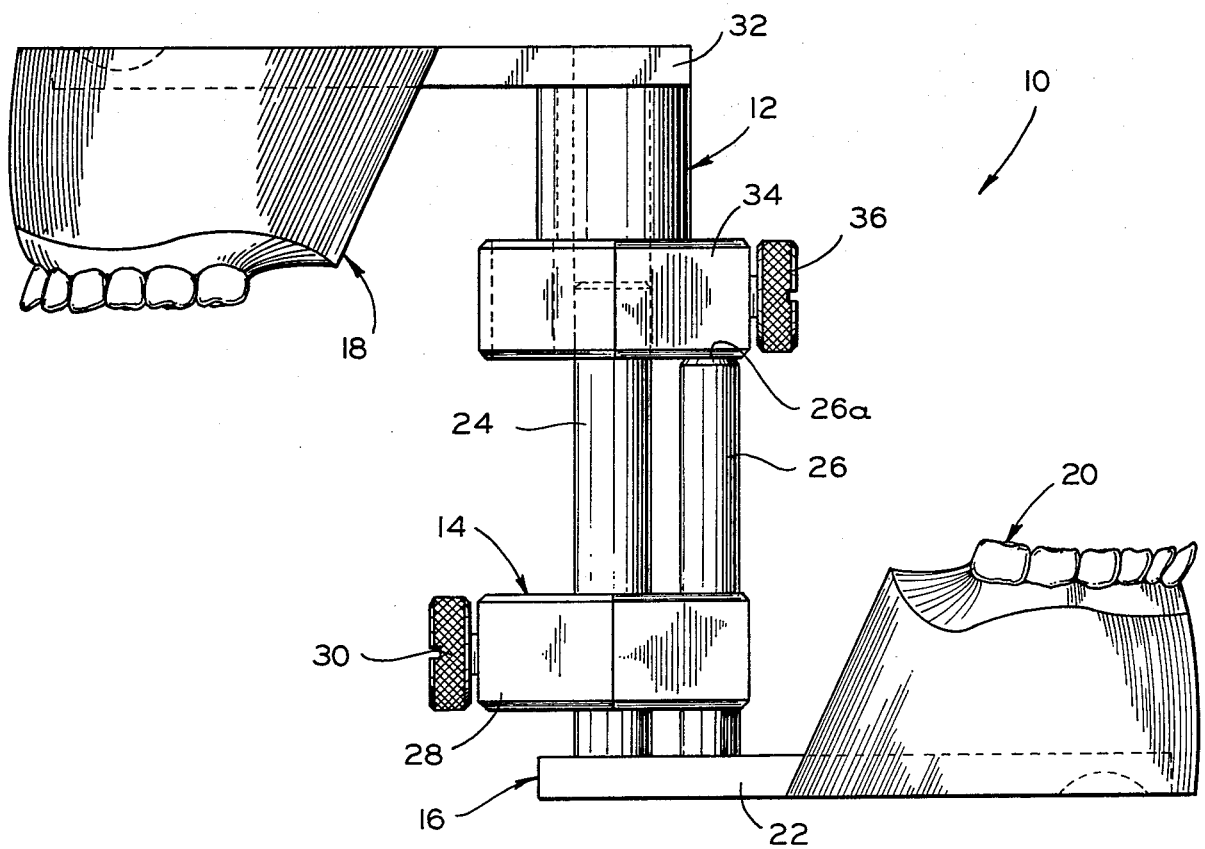
FIG. 4 is a side elevational view illustrating the upper arm in a pivoted position relative to the lower arm.

As long as the cylindrical guide shafts 24 and 26 are inserted within the aperture 34a and 34b, respectively the upper arm assembly 16 can only move vertically relative to the lower arm assembly 12. However, when the lower surface 34c of the mounting device 34 has been raised above the upper end 26a of the guide shaft 26, the upper arm assembly 16 can pivot about the guide shaft 24, as shown in FIG. 4. This enables the technician to work with the lower dental casting 18 while not having to completely remove the upper arm assembly from the apparatus 10. If the technician desires to work with the upper dental casting 20, the entire apparatus 10 can be inverted from the position shown in FIG. 4 such that the apparatus 10 is supported by the surface 32b of the upper arm 32.

In accordance with the provisions of the patent statutes, the principles and mode of operation of the present invention have been described in what is considered to represent its preferred embodiment. However, it should be understood that the invention may be practiced otherwise and as specifically illustrated and described without departing from its spirit or scope.

What is claimed is:

1. An apparatus for use in fabricating orthodontic appliances comprising:
   a pair of spaced apart lower and upper horizontally extending arms, said lower arm adapted to carry a lower dental casting and said upper arm adapted to carry an upper dental casting in facing relationship with the lower dental casting;
   a guide member attached to said lower arm and extending upwardly in a generally vertical direction;
   means for mounting said upper arm on said guide member for vertical movement toward and away from said lower arm, said mounting means including means for preventing any rotative movement of said upper arm relative to said lower arm about said guide member when said upper arm is spaced less than a predetermined distance from said lower arm, and permitting pivotal movement of said upper arm relative to said lower arm about said guide member when said upper arm is spaced more than the predetermined distance from said lower arm; and
   reference stop means slidably mounted on said guide member between said lower arm and said upper arm and including means for releasably securing said stop means on said guide member in a selected vertical position relative to said lower arm, said stop means engageable with said mounting means for limiting the spacing between said upper arm and said lower arm.

2. The invention defined in claim 1 including means for releasably securing said upper arm on said guide member in a selected vertical position relative to said lower arm.

3. The invention defined in claim 1 wherein said guide member includes a pair of spaced apart parallel cylindrical guide shafts attached to said lower arm and extending upwardly in a generally vertical direction and said mounting means includes a pair of spaced apart cooperating guide apertures for slidably receiving said guide shafts.

4. The invention defined in claim 3 wherein one of said guide shafts extends upwardly past the upper end of the other one of said guide shafts.

5. An apparatus for use in fabricating orthodontic appliances comprising:
   a pair of spaced apart lower and upper horizontally extending arms, said lower arm adapted to carry a lower dental casting and said upper arm adapted to carry an upper dental casting in facing relationship with the lower dental casting;
   a pair of spaced apart parallel cylindrical guide shafts attached to said lower arm and extending upwardly in a generally vertical direction, one of said guide shafts extending upwardly past the upper end of the other one of said guide shafts;
   means for mounting said upper arm on said guide shafts for vertical movement toward and away from said lower arm, said mounting means including a pair of spaced apart cooperating guide apertures for slidably receiving said guide shafts;
   means for releasably securing said upper arm on said guide shafts in a selected vertical position relative to said lower arm; and
   reference stop means having at least one aperture formed therein for slidably receiving at least one of said guide shafts, said reference stop means positioned on said one guide shaft between said lower arm and said upper arm and including means for releasably securing said stop means on said one guide shaft in a selected vertical position relative to said lower arm, said stop means engageable with said mounting means for limiting the spacing between said upper arm and said lower arm.

* * * * *